United States Patent [19]

Alexander et al.

[11] Patent Number: 4,729,989

[45] Date of Patent: * Mar. 8, 1988

[54] ENHANCEMENT OF ABSORPTION OF DRUGS FROM GASTROINTESTINAL TRACT USING CHOLINE ESTER SALTS

[75] Inventors: Jose Alexander; Joseph A. Fix, both of Lawrence, Kans.

[73] Assignee: Merck & Co., Inc., Rahway, N.J.

[*] Notice: The portion of the term of this patent subsequent to Sep. 8, 2004 has been disclaimed.

[21] Appl. No.: 749,696

[22] Filed: Jun. 28, 1985

[51] Int. Cl.[4] .................... A61K 31/43; A61K 31/545
[52] U.S. Cl. ..................... 514/192; 514/193; 514/194; 514/195; 514/196; 514/197; 514/198; 514/199; 514/200; 514/201; 514/202; 514/203; 514/204; 514/205; 514/206; 514/207; 514/208; 514/209; 514/946; 514/947
[58] Field of Search ................ 514/3, 4, 946, 947, 514/192, 200, 201, 209, 193, 194, 195, 196, 197, 198, 199, 202, 203, 204, 205, 206, 207, 208

[56] References Cited

U.S. PATENT DOCUMENTS

| | | | |
|---|---|---|---|
| 4,035,486 | 7/1977 | Laborit | 514/4 |
| 4,425,337 | 1/1984 | Alexander et al. | 424/181 |
| 4,462,991 | 7/1984 | Higuchi | 424/177 |

FOREIGN PATENT DOCUMENTS 5976024  10/1982  Japan ..................... 514/3

OTHER PUBLICATIONS

George et al., *J. Infect. Dis.*, 136, 822 (1977).
Cassidy et al., *J. Cell Biol.*, 32, 672 (167).
Yaginuma et al., *Chem. Pharm. Bull.*, 29, 1974 (1981).

*Primary Examiner*—Frederick E. Waddell
*Attorney, Agent, or Firm*—Manfred Polk; Michael C. Sudol, Jr.

[57] ABSTRACT

Choline ester salts are used as drug absorption enhancing agents for orally and rectally administered drugs.

3 Claims, No Drawings

ENHANCEMENT OF ABSORPTION OF DRUGS FROM GASTROINTESTINAL TRACT USING CHOLINE ESTER SALTS

BACKGROUND OF THE INVENTION

The invention relates to novel compositions and methods for enhancing absorption of drugs from the gastrointestinal tract by incorporating therein a choline ester salt absorption enhancing agent.

DESCRIPTION OF THE PRIOR ART

Though the gastrointestinal tract is the preferred route for drug delivery, all drugs are not well absorbed from this site. In many cases, this may be due to the polar nature or hydrophilic character of the drugs. Since they are precluded from rapid absorption, such drugs are subject to long residency time in the gastrointestinal environment where both acidic and enzymatic degradation contribute to their poor bioavailability. It is, therefore, clear that any factor which enhances the rate of absorption will demonstrate improved clinical efficacy. In recent years, considerable effort has been directed toward identifying agents which increase gastrointestinal absorption of poorly absorbed drugs. For example, surface active agents (George, Sutter, Finegold, J. Infect. Dis. 136, 822 (1977), chelating agents (Cassidy, Tidball, J. Cell Biol. 32, 672 (1967), salicylates (Higuchi, et al., U.S. Pat. No. 4,462,991 (1984)), antiinflammatory agents (Yaginuma et al., Chem. Pharm. Bull. 29, 1974 (1981) and phenothiazines (Alexander and Fix, U.S. Pat. No. 4,425,337 (1984) have been shown to increase gastrointestinal permeability of a variety of drugs.

The present use of choline esters to promote gastrointestinal absorption affords several advantages over the prior art's absorption promoting compounds. The choline esters, especially those with medium and long chain fatty acid components, are more potent than the presently used absorption promoting agents. As an example, in aqueous solutions, the choline esters are effective absorption promoting agents at levels as low as 0.05%. By contrast, the effective dose of other known absorption promoters is significantly higher: sodium salicylate—1%, surfactants—1%, chelating agents—2%. This difference in potency affords opportunities for reducing the required size of the dosage form and potentially minimizing side effects. The choline esters cause reversible changes in gastrointestinal permeability to the target drug, indicating that a permanent change has not occurred. Other promoting agents, such as the surfactants, cause a relatively permanent change in gastrointestinal permeability, which is only overcome by turnover of the mucosal cells, a process which may require days for completion. By contrast, removal of choline esters from the gastrointestinal tract results in reversion to normal permeability properties in less than 2 hours. This provides a significant advantage in that a rapid and reversible increase in drug absorption does not allow prolonged intervals during which potentially toxic or otherwise harmful agents might also be absorbed. Another potential advantage of the choline esters is that, unlike chelating agent such as EDTA, the choline esters may not necessarily sequester divalent cations ($Mg^{++}$ or $Ca^{++}$) which are necessary for the normal functioning of cells. In other words, there is no tissue damage at concentrations of choline esters which significantly increase drug absorption. In contrast to this, studies have indicated that surfactant activity, as with sodium lauryl sulfate, is generally associated with some degree of cellular damage. This lack of tissue damage affords a significant advantage to the use of choline esters in promoting gastrointestinal drug absorption. An added advantage is that they can be metabolized through normal pathways in the body. Thus, on enzymatic hydrolysis the choline esters produce choline and a fatty acid, both of which are normal endogenous components and nutritive agents. This eliminates a potential problem of introducing substances which are not normally present in the biochemical pathways of the body (e.g. salicylates, EDTA, etc.)

SUMMARY OF THE INVENTION

It has been found that when poorly absorbed drugs are administered orally or rectally, the bioavailability of said drugs is increased by incorporating therein a choline ester salt absorption enhancing agent.

Accordingly, it is an object of this invention to enhance the bioavailability of poorly absorbed drugs administered orally or rectally by administering therewith a choline ester absorption enhancing agent.

A further object of the invention is to provide a new dosage form utilizing a class of choline esters which when administered orally or rectally with a therapeutic agent will provide an increased blood level of said therapeutic agent.

Another object of the invention is to provide a choline ester absorption promoter of gastrointestinal and rectal drug absorption at concentrations which do not alter the normal morphology of the mucosal cells.

Still another object of the invention is to provide a choline ester series of absorption enhancing agents that are endogenous and can be metabolized through normal pathways available in the body.

Other objects, features and advantages of the invention will be apparent to those skilled in the art from the detailed description of the invention which follows.

All of the foregoing objects are readily attained by providing a composition and method wherein oral and rectal absorption of poorly absorbed drugs is enhanced. The method comprises the steps of preparing a dosage form suitable for oral or rectal delivery, and a dosage form comprising an effective unit dosage amount of the poorly absorbed drug, a choline ester salt absorption agent, the agent being present in said dosage form in an amount sufficient to be effective in enhancing the rate of the oral and rectal absorption of the therapeutic agent, and pharmaceutically acceptable excipients.

DETAILED DESCRIPTION OF THE INVENTION

The present invention is directed to a method of enhancing the rate of gastrointestinal absorption of an orally or rectally administered drug. The method generally comprises administering a dosage form capable of being orally or rectally administered, wherein the dosage form comprises a therapeutically effective dosage amount of a poorly absorbed drug and a choline ester salt absorption enhancing agent, the choline ester being present in the dosage form in a sufficient quantity to be effective in enhancing oral and rectal absorption rates.

The compounds that are used as absorption enhancers in our method and compositions are choline fatty acid ester salts of the formula:

$$[(CH_3)_3N^+CH_2CH_2OR]X^-$$

wherein R is:

(a) $C_2$–$C_{20}$ saturated acyl such as acetyl, hexanoyl, octanoyl, decanoyl, lauroyl, myristoyl, palmitoyl, stearoyl and the like;

(b) $C_2$–$C_{20}$ acyl with 1 to 6 double bonds such as 2-hexenoyl, 9-decenoyl, 9-hexadecenoyl (palmitoleoyl), oleoyl, myristoleoyl, 9,12-hexadecadienoyl, α-linoleoyl, γ-linolenoyl, arachidoyl and the like;

(c) $C_2$–$C_{20}$ hydroxyacyl with 1 to 3 hydroxy groups such as 2-hydroxylauroyl, 2-hydroxymyristoyl, 2-hydroxypalmitoyl and the like;

(d) $C_4$–$C_{20}$ ketoacyl such as 6-ketodecanoyl, 4-keto-9,11,13-octadecatrienoyl and the like;

(e) $C_5$14 $C_{20}$ unsaturated hydroxyacyl such as 2-hydroxy-12-octadecenoyl and the like;

(f) $C_5$–$C_{20}$ carbalkoxyacyl such as ω-ethoxy-carbonyloctanoyl and the like;

(g) $C_4$–$C_{20}$ carboxy acyl such as ω-carboxy undecanoyl;

and $X^-$ is a pharmaceutically acceptable counterion such as chloride, sulfate, nitrate, perchlorate, bromide, iodide, phosphate, acetate, benzoate, tartrate, citrate, propionate, gluconate, lactate, maleate, fumarate, bezylate, camsylate, esylate, gluceptate, mesylate, napsylate and the like.

The preferred oral and rectal absorption enhancing agents of the above formula are:
1. hexanoylcholine
2. lauroylcholine
3. octanoylcholine
4. myristoylcholine
5. palmitoylcholine
6. stearoylcholine
7. 2-hexenoylcholine
8. 9-decenoylcholine
9. 9-hexadecenoylcholine
10. α-lineoylcholine
11. 2-hydroxylauroylcholine
12. 6-ketodecanoylcholine
13. ω-ethoxycarbonyloctanoylcholine
14. 2-hydroxypalmitoylcholine The most preferred absorption enhancing agents useful in our method and dosage forms are:
1. hexanoylcholine
2. octanoylcholine
3. decanoylcholine
4. lauroylcholine
5. myristoylcholine
6. palmitoylcholine
7. stearoylcholine The choline ester salt absorption enhancing agents employed in the practice of this invention are known compounds which are commercially available and processes for their preparation are disclosed throughout the art.

Various active agents provide beneficial effects when administered to patients. Such agents which can be made more useful by enhancing their absorption in accordance with this invention, are exemplified by, but not limited to, the following classes of drugs:

1) β-lactam antibiotics such as cefoxitin, N-formamidinyltheinamycin, ampicillin, azlocilin, bacampicillin, carbenicillin, cefaclor, cefadroxil, cefamandole, cefatrizine, cefazoline, cefonicid, cefaperazone, ceforanide, cefotaxime, cefotiam, cefroxadine, cefsulodin, ceftazidime, ceftriaxone, ceftizoxime, cephalexin, cephaloglycin, cephaloridine, cephradine, cyclacillin, cloxacillin, dicloxacillin, floxacillin, hetacillin, methicillin, nafcillin, oxacillin, sarmoxacillin, sarpicillin, talampicillin, ticaricillin, penicillin G., penicillin V., pivampicillin, piperacillin, pirbenicillin and the like.

(2) Aminoglycoside antibiotics such as gentamycin, amikacin, astromicin, betamicin, butikacin, butirosin, clindamycin, josamycin, kanamycin, neomycin, netilmicin, tobramycin and the like.

(3) Antiviral agents such as ara C (cytarabine), acyclovir, floxuridine, ribavirin, vidarabine, idoxuridine, trifluridine and the like.

(4) Amino acids such as methyldopa, carbidopa, levodopa, fludalanine, γ-aminobutyric acid and the like.

(5) Smooth muscle relaxants such as theophylline, aminophylline, diphylline, oxtriphylline, ambuphylline, fenethylline, guathylline, pentoxyfylline, xanthinol niacinate, glucophylline and the like.

(6) Polypeptides such as cyclo(N-Ala-Tyr-D-Trp-Lys-Val-Phe) acetate, somatostatin, inslulin, gastrin, caerulein, cholecystokinin and the like.

(7) Anti-inflammatory agents such as indomethacin, sulindac, ibuprofen and the like.

(8) Diruetics such as aldactone, hydrochlorothiazide, amiloride, chlorothiazide, furosemide and the like.

The enhancement of drug absorption in accordance with this invention is not by any means limited to the above drugs, but are in general applicable to other classes of drugs such as analgesics, anabolics, androgens, anorexics, adrenergics, antiadrenergics, antiallergics, antibacterials, anticholinergics, antidepressants, antidiabetics, antifungal agents, antihypertensives, antineoplastics, antipsychotics, sedatives, cardiovascular agents, antiulcer agents, anticoagulants, anthelmintics, radio-opaques, radionuclide diagnostic agents and the like.

The amount of poorly absorbed drug varies over a wide range, however the therapeutically effective unit dosage amount of the selected poorly absorbed drug depends on that amount known in the art to obtain the desired results.

Generally, the amount of adjuvant employed in the practice of the invention ranges from 0.05–500 mg in each unit dose. The percentage of adjuvant in the total combination of drug plus adjuvant is 0.05–50% with a preferred ratio of adjuvant in the total combination of adjuvant plus drug being 0.5–25%. The remaining percent being the drug and optionally other excipients.

For oral administration, the formulations may be prepared as liquids, suspensions, capsules, tablets, coated tablets, and other standard procedures known in the art. The preferred formulation is a compressed tablet composed of a minimum of 1 mg choline ester with the pharmacologically required dose of drug and sufficient excipients to formulate an acceptable composition.

For rectal application, the formulations may be prepared as microenemas, suppositories, rectal tablets, and other standard procedures known in the art. The preferred formulation is a solid suppository composed of a minimum of 1 mg choline ester with the pharmacologically required dose of drug and sufficient suppository base to formulate an acceptable composition. The methods and choice of excipients and suppository bases are well known to those skilled in the art and the composition of said formulations is not limited to compressed tablets or solid suppositories by this invention.

The following examples illustrate preparation of various compositions of the invention. The examples should be construed as illustrations rather than limitations thereof.

EXAMPLE 1

Effect of lauroyl choline chloride and palmitoyl choline iodide on the rectal absorption of drug entities Experiments were performed with rats wherein each animal received an aqueous microenema applied to the rectal cavity. The microenemas contained target drug entity (amount shown in table) in the presence or absence of 5 mg lauroylcholine chloride or palmitoylcholine iodide. Blood levels were monitored and the amount of drug absorbed calculated against intravenous administration and expressed as percent bioavailability.

| Target Drug | Dose | Drug Class | choline Control | Percent Bioavailability (mean ± SD) with | |
|---|---|---|---|---|---|
| | | | | Lauroyl choline chloride | Palmitoyl choline iodide |
| Sodium cefoxitin | 2.5 mg | β-lactam antibiotic | 2 ± 1.1 | 100 ± 13.2 | 56 ± 4.1 |
| Gentamicin sulfate | 2.5 mg | aminoglycoside antibiotic | 4 ± 1.2 | 132 ± 43.3 | — |
| Cytarabine | 2.5 mg | anti-viral anti-neoplastic | 0.5 ± 0.1 | 71 ± 8.5 | 51 ± 8 |
| *Theophylline | 2.5 mg | smooth muscle relaxant | 75 ± 3.3 | 66 ± 4.9 | 36 ± 3.4 |
| ** | 0.1 mg | polypeptide | 7 ± 3.5 | 132 ± 43.3 | 27 ± 9.8 |
| Methyldopa | 2.5 mg | cardiovascular antihypertensive | 6 ± 0.3 | 90 ± 15.5 | 45 ± 12.8 |

**cyclo(N—Me—Ala—Tyr—D-Trp—Lys—Val—Phe)acetate
*(comparison example). The drug is absorbed well by itself.

EXAMPLE 2

Effect of various choline esters on rectal absorption of sodium cefoxitin, a β-lactam antibiotic, and cyclo(N-Ala-Tyr-D-Trp-Lys-Val-Phe)acetate, a polypeptide Each animal received an aqueous microenema, pH 6, containing 2.5 mg sodium cefoxitin or 0.1 mg cyclo(N-Ala-Try-D-Trp-Lys-Val-Phe)-acetate and 5.0 mg various choline esters of the general formula of this invention. Blood samples were collected and sodium cefoxitin or cyclo(N-Ala-Try-D-Trp-Lys-Val-Phe)acetate assayed. The amount of drug absorbed is expressed as percent bioavailability versus intravenous administration

| | Percent Bioavailability (mean ± SD) | |
|---|---|---|
| Choline Ester Salt | Sodium Cefoxitin* | ** |
| None | 2 ± 1.1 | 7 ± 3.5 |
| Lauroylcholine-Cl | 100 ± 13.2 | 132 ± 43.3 |
| Myristoylcholine-Cl | 32 ± 4.6 | 100 ± 45.0 |
| Palmitoylcholine-I | 56 ± 4.1 | 27 ± 9.8 |
| Stearoylcholine-I | 27 ± 6.8 | 26 ± 5.1 |

*β-lactam antibiotic
**Cyclo(N—Ala—Try—D-Trp—Lys—Val—Phe)acetate

EXAMPLE 3

Importance of choline palimitoyl ester linkage in absorption promoting effects on rectal sodium cefoxitin absorption Each animal received an aqueous microenema, pH 6, containing 2.5 mg sodium cefoxitin in the presence or absence of 5.0 mg palmitic acid, choline or palmitoylcholine iodide. Blood was collected and sodium cefoxitin measured. Absorption of sodium cefoxitin is expressed as percent bioavailability versus intravenous administration.

| Compound | Sodium Cefoxitin Percent Bioavailability (mean ± SD) |
|---|---|
| None | 2 ± 1.1 |
| Palmitic acid | 1 ± 0.8 |
| Choline | 1 ± 0.6 |
| Palmitoylcholine-I | 56 ± 4.1 |

EXAMPLE 4

Reversibility of absorption promoting effect of choline esters

Two separate experiments with two choline esters demonstrate that these esters cause no permanent change in rectal mucosal tissue at concentrations which effectively increase drug absorption. In these experiments animals are treated with 5.0 mg of lauroylcholine-Cl or palmitoylcholine-I alone and then tested for sodium cefoxitin absorption either immediately or after 1 hour or 2 hours of recovery. Sodium cefoxitin absorption is expressed as percent bioavailability and indicates the reversibility of the absorption promoting effect upon removal of the choline ester.

| Interval Between Administrations (min) | Sodium Cefoxitin Percent Bioavailability | |
|---|---|---|
| | with Lauroyl choline Chloride | with Palmitoylcholine iodide |
| 0 | 100 ± 13.2 | 56 ± 4.1 |
| 60 | 24 ± 2.8 | 1 ± 0.5 |
| 120 | 5 ± 6.2 | 10 ± 1.7 |

EXAMPLE 5

Effect of choline esters on small intestinal absorption of polypeptides

Experiments were performed with rats wherein each animal received an aqueous solution applied to the duodenal region. The solutions contained target drug entity 0.1 mg [cyclo(N-Ala-Try-D-Trp-Lys-Val-Phe)acetate] in the presence or absence of 5 mg of choline esters. Blood levels were monitored and the amount of polypeptide absorbed calculated against intravenous administration and expressed as percent bioavailability.

| Adjuvant | Percent Bioavailability (mean ± SD) of ** |
|---|---|
| None | 1 |
| Lauroylcholine chloride | 8.6 ± 1.4 |
| Palmitoylcholine chloride | 6 ± 2 |

**Cyclo(N—Ala—Try—D-Trp—Lys—Val—Phe)acetate

EXAMPLE 6

Effect of choline esters on small intestinal absorption of cofoxitin

Experiments were performed as in Example 5. The solutions contained 10 mg/kg of cefoxitin and 20 mg/kg of absorption promoters. Blood levels of cefoxitin were monitored and the bioavailability of cefoxitin absorbed was calculated against intravenous administration.

| Adjuvant | Percent Bioavailability (mean ± SD) of cefoxitin |
| --- | --- |
| None | 2 ± 1.1 |
| Myristoylcholine chloride | 32 ± 4.6 |
| Stearoylcholine iodide | 20.3 ± 5.9 |

What is claimed is:

1. A method of enhancing the rate of gastrointestinal absorption of an orally or rectally administred drug, comprising administering a dosage form capable of being orally or rectally absorbed, said dosage form comprising a therapeutically effective dosage amount of a poorly absorbed β-lactam antibiotic drug selected from the group consisting of cefoxitin, N-formamidinyltheinamycin, ampicillin, azlocillin, bacampicillin, carbenicillin, cefaclor, cefadroxil, cefamandole, cefatrizine, cefazoline, cefonicid, cefaperazone, ceforanide, cefotaxime, cefotiam, cefroxadine, cefsulodin, ceftazidime, ceftriaxone, ceftizoxime, cephalexin, cephaloglycin, cephaloridine, cephradine, cyclacillin, cloxacillin, dicloxacillin, floxacillin, hetacillin, methicillin, nafcillin, oxacillin, sarmoxacillin, sarpicillin, talampicillin, ticarcillin, penicillin G., penicillin V., pivampicillin. piperacillin, pirbenicillin and a choline ester absorption enhancing agent of the formula :

$$[(CH_3)_3N^+CH_2CH_2OR]X^-$$

wherein R is saturated acyl ($C_2$–$C_{20}$), acyl($C_2$–$C_{20}$) with 1 to 6 double bonds, hydroxyacyl($C_2$–$C_{20}$) with 1 to 3 hydroxy groups, ketoacyl($C_4$–$C_{20}$), unsaturated hydroxycacyl($C_5$–$C_{20}$) or carbalkoxyacyl($C_5$–$C_{20}$), or carboxy acyl($C_4$–$C_{20}$) and X- is a pharmaceutically acceptable counterion.

2. The method of claim 1 wherein said drug is cefoxitin, N-formamidinyltheinamycin, cephalexin or cefaclor and said agent is selected from the group consisting of hexanoylcholine, octanoylcholine, decanoylcholine, lauroylcholine, myristoylcholine, palmitoylcholine, stearoylcholine, 2-hexenoylcholine, 9-decenoylcholine, 9-hexadecenoylcholine, α-linoleoylcholine, 2-hydroxylauroylcholine, 2-hydroxymyristoylcholine, 6-ketodecanoylcholine, 12-hydroxy-12-octadecenoylcholine, ω-ethoxycarbonyloctanoylcholine and 2-hydroxypalmitoylcholine.

3. The method of claim 2, wherein said agent is a salt selected from the group consisting of hexanoylcholine, octanoylcholine, decanoylcholine, lauroylcholine, myristoylcholine, palmitoylcholine and stearoylcholine.

* * * * *